US012765990B2

(12) United States Patent
Poulos et al.

(10) Patent No.: US 12,765,990 B2
(45) Date of Patent: Oct. 20, 2026

(54) IMPLANT DEVICE FOR PLANTAR REPAIR

(71) Applicants: VIRGINIA TECH INTELLECTUAL PROPERTIES, INC., Blacksburg, VA (US); CARILION CLINIC, Roanoke, VA (US)

(72) Inventors: Demitria Poulos, Knoxville, TN (US); Logan N. Dickinson, Blacksburg, VA (US); Skye Carlson, Cleveland Heights, OH (US); Zachary Kozar, Leesburg, VA (US); Jennifer S. Wayne, Blacksburg, VA (US); Vincent Wang, Blacksburg, VA (US); John R. Clements, Roanoke, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 426 days.

(21) Appl. No.: 18/555,383

(22) PCT Filed: May 4, 2022

(86) PCT No.: PCT/US2022/027654
§ 371 (c)(1),
(2) Date: Oct. 13, 2023

(87) PCT Pub. No.: WO2022/235787
PCT Pub. Date: Nov. 10, 2022

(65) Prior Publication Data
US 2024/0207041 A1 Jun. 27, 2024

Related U.S. Application Data

(60) Provisional application No. 63/184,563, filed on May 5, 2021.

(51) Int. Cl.
*A61F 2/08* (2006.01)

(52) U.S. Cl.
CPC ..... *A61F 2/0811* (2013.01); *A61F 2002/0835* (2013.01); *A61F 2002/0852* (2013.01);
(Continued)

(58) Field of Classification Search
CPC ............ A61F 2/0811; A61F 2002/0835; A61F 2002/0852; A61F 2002/0882;
(Continued)

(56) References Cited

U.S. PATENT DOCUMENTS 11,045,305 B2 * 6/2021 Blacklidge ......... A61B 17/8875
2006/0264932 A1 11/2006 Bert
(Continued)

OTHER PUBLICATIONS

International Search Report and Written Opinion for PCT/US2022/027654 mailed Aug. 30, 2022.

*Primary Examiner* — Bruce E Snow
(74) *Attorney, Agent, or Firm* — Perilla Knox & Hildebrandt LLP; Stephanie L. Davy-Jow; Jason M. Perilla

(57) ABSTRACT

Various aspects of an implant for plantar plate repair and a surgical method of plantar plate repair using the implant are described. In one example, the implant includes a female component and a male component. The female component includes an open barrel having an outer surface and an inner surface, a flange cap at one end of the open barrel, and a recessed tiedown bar that extends between openings through the flange cap. The openings through the flange cap extending into the open barrel of the female component. The male implant includes an open barrel portion, a pair of fingers extending from one end of the open barrel portion, and a flange cap at another end of the open barrel portion. The male implant also includes an opening through the flange
(Continued)

cap, extending into the open barrel portion of the male implant.

18 Claims, 8 Drawing Sheets

(52) U.S. Cl.
CPC ................. *A61F 2002/0882* (2013.01); *A61F 2220/0033* (2013.01); *A61F 2220/0075* (2013.01)

(58) Field of Classification Search
CPC ...... A61F 2220/0033; A61F 2220/0075; A61F 2002/0823; A61F 2220/0025
See application file for complete search history.

(56) References Cited

U.S. PATENT DOCUMENTS

| | | | |
|---|---|---|---|
| 2009/0228049 | A1 | 9/2009 | Park |
| 2010/0331896 | A1 | 12/2010 | Le Couedic et al. |
| 2018/0368969 | A1 | 12/2018 | Martini et al. |
| 2019/0350695 | A1 | 11/2019 | Blacklidge et al. |
| 2024/0207041 | A1* | 6/2024 | Poulos .................. A61F 2/0811 |

* cited by examiner

IMPLANT DEVICE FOR PLANTAR REPAIR

CROSS REFERENCE TO RELATED APPLICATIONS

This application is a 371 U.S. National Stage Application of PCT Application Serial Number PCT/US2022/027654 filed on May 4, 2022, which application claims the benefit of and priority to U.S. Provisional Application No. 63/184,563, filed May 5, 2021, titled "IMPLANT DEVICE FOR PLANTAR REPAIR," the entire contents of each which are hereby incorporated herein by reference.

BACKGROUND

The plantar plate is a fibrocartilaginous structure located at the underside of the forefoot. A plantar plate tear is a common injury that may occur with excessive force and trauma to the forefoot. This injury can cause immense discomfort and pain, as well as alter the appearance of the toe. Surgery is recommended in many cases to repair the plantar plate. Individuals that experience plantar plate tears are commonly young athletes, women, and elderly patients.

Conventional techniques for plantar plate repair can lead to postoperative complications, such as phalanx fracture, avascular necrosis, and other complications. Although the main cause for fracture and avascular necrosis is unknown, surgeons have hypothesized that a suture sawing effect on the dorsal side of the phalanx may be the root of the problem. This sawing effect is due to a combination of the suture tension and the repetitive compressive and tensile loads applied to the fixation site. These loads induce a repetitive friction force on the outer surface of the phalanx, which can grind down the hard cortical bone and increase the likelihood of fracture. The postoperative complications can lead to continuous pain and discomfort, alter the appearance of the toe, or result in loss of toe function. This can be disappointing for both the patient and the surgeon.

SUMMARY

In one embodiment, an implant for plantar repair includes a female component and a male component. The female component includes an open barrel having an outer surface and an inner surface, a female flange cap at one end of the open barrel, openings through the female flange cap, extending into a center of the open barrel, and a recessed tiedown bar that extends between the openings through the female flange cap. The male component includes an open barrel portion having an outer surface, a pair of fingers extending from one end of the open barrel portion, a male flange cap at another end of the open barrel portion, and an opening through the male flange cap, extending into the open barrel portion.

In other aspects of the embodiments, the female component further includes female interlocking features formed into at least a portion of the inner surface of the female component. The male component further includes male interlocking features formed into outer surfaces of the pair of fingers. The male interlocking features snap and interlock into the female interlocking features within the open barrel of the female component.

In other aspects, an outer peripheral surface of the male flange cap extends a radial distance away from a central longitudinal axis of the male component further than the outer surface of the open barrel portion. Additionally, an outer peripheral surface of the female flange cap extends a radial distance away from a central longitudinal axis of the female component further than the outer surface of the open barrel. The female component and the male component are formed from polyether ether ketone in one case, although other materials can be relied upon.

In another embodiment, a method of plantar repair, includes installing an implant for plantar repair into a phalanx bone of a foot, passing a suture through a plantar plate at a plantar side of the foot, passing ends of the suture through the implant, and securing the ends of the suture at a dorsal side of the foot, with a knot secured against the implant at the dorsal side of the foot.

Installing the implant can include forming an incision in the dorsal side of a foot above the phalanx bone and in the plantar side of the foot below the phalanx bone, drilling a hole through the phalanx bone, inserting a female component of a plantar repair implant into the phalanx, from the dorsal side of the foot, and pushing the male component, from the plantar side, toward the female component, to snap the male component into the female component.

Installing the implant can also include inserting suture passing wires through the female component from the dorsal side, extending to the plantar side of the foot, sliding the suture passing wires through the male component of the plantar repair implant, at the plantar side, holding the female component in place from the dorsal side, and pushing the male component, from the plantar side, toward the female component, to snap the male component into the female component, with the suture passing wires extending through the implant. The method can also include passing ends of the suture through the suture passing wires at the dorsal side of the foot, and pulling the ends of the sutures through the implant using the suture passing wires.

In the method of plantar plate repair, the implant can include a female component and a male component. The female component can include an open barrel having an outer surface and an inner surface, a female flange cap at one end of the open barrel, openings through the female flange cap, extending into a center of the open barrel, and a recessed tiedown bar that extends between the openings through the female flange cap. With this implant, securing the ends of the suture can include securing the ends of the suture at a dorsal side of the foot, with a knot secured against the recessed tiedown bar at the dorsal side of the foot.

The male component can include an open barrel portion having an outer surface, a pair of fingers extending from one end of the open barrel portion, a male flange cap at another end of the open barrel portion, and an opening through the male flange cap, extending into the open barrel portion. The female component further includes female interlocking features formed into at least a portion of the inner surface of the female component, and the male component further includes male interlocking features formed into outer surfaces of the pair of fingers. With this implant, installing the implant includes snapping the male interlocking features into the female interlocking features.

BRIEF DESCRIPTION OF THE DRAWINGS

Many aspects of the present disclosure can be better understood with reference to the following drawings. The components in the drawings are not necessarily drawn to scale, with emphasis instead being placed upon clearly illustrating the principles of the disclosure. In the drawings, like reference numerals designate corresponding parts throughout the several views.

DETAILED DESCRIPTION

Figure 1:
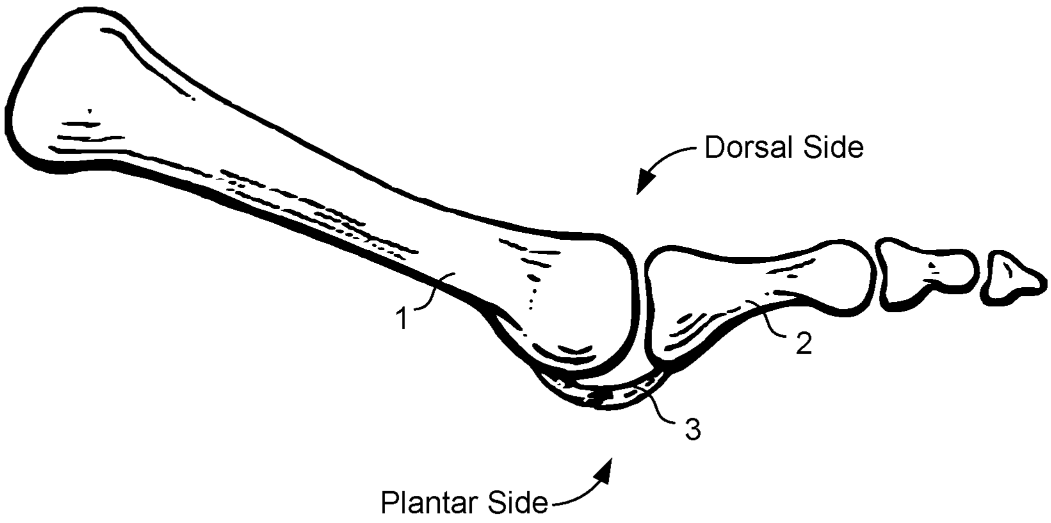
FIG. 1 illustrates an example metatarsal bone and proximal phalanx bone of the foot according to various examples described herein.

As noted above, conventional techniques for plantar plate repair can lead to postoperative complications, such as phalanx fracture, avascular necrosis, and other complications. Although the main cause for fracture and avascular necrosis is unknown, surgeons have hypothesized that a suture sawing effect on the dorsal side of the phalanx may be the root of the problem. This sawing effect is due to a combination of the suture tension and the repetitive compressive and tensile loads applied to the fixation site. These loads induce a repetitive friction force on the outer surface of the phalanx, which can grind down the hard cortical bone and increase the likelihood of fracture. The postoperative complications can lead to continuous pain and discomfort, alter the appearance of the toe, or result in loss of toe function.

In view of the concerns outlined above, one objective of the embodiments is to create a durable solution for plantar plate tears, one that avoids the suture sawing effect and provides other benefits. The embodiments described herein are directed to an implant for plantar plate repair. The implant can be relied upon to provide a more robust solution for plantar plate repair, reduce or eliminate the dorsal saw effect, and minimize common postoperative complications. In one example, the implant includes a female component and a male component. The female component includes an open barrel having an outer surface and an inner surface, a flange cap at one end of the open barrel, and a recessed tiedown bar that extends between openings through the flange cap. The openings through the flange cap extend into the open barrel of the female component. The male implant includes an open barrel portion, a pair of fingers extending from one end of the open barrel portion, and a flange cap at another end of the open barrel portion. The male implant also includes an opening through the flange cap, extending into the open barrel portion of the male implant.

As described in further detail below, the implant is adjustable and capable of adapting to the size of the phalanx one of a patient based on a snap-fit design of the implant. The design uses a two-piece implant that sits in the phalanx to secure a sterile surgical thread or sutures and repair torn or otherwise injured plantar plates. When installed, a flange cap of the female component of the implant sits or rests upon the top, dorsal side of the the phalanx bone, while a flange cap of the male component of the implant sits or rests upon the bottom, plantar side of the phalanx bone. Extending through the bone, the male and female components fit together with a variable height snapping mechanism. A suture can be passed or stitched through the plantar plate at the plantar side of the foot, passed through the implant installed in the phalanx bone, and tied or secured with a knot at the dorsal side of the foot. The female component includes a recessed tiedown bar, and the suture can be tied over the tiedown bar. The tiedown bar provides an alterative position to secure the suture at the top of the phalanx bone, without a need to secure or tie the suture upon the phalanx bone itself.

In other embodiments, a method of plantar plate repair is described. The method includes installing an implant for plantar plate repair into a phalanx bone of a foot, passing a suture through a plantar plate at a plantar side of the foot, passing ends of the suture through the implant, and securing the ends of the suture at a dorsal side of the foot, with a knot secured against the implant at the dorsal side of the foot. Installing the implant can include forming an incision in the dorsal side of a foot above the phalanx bone and in the plantar side of the foot below the phalanx bone, drilling a hole through the phalanx bone, inserting a female component of a plantar repair implant into the phalanx, from the dorsal side of the foot, and pushing the male component, from the plantar side, toward the female component, to snap the male component into the female component.

In other aspects of the method, the implant includes a female component and a male component, and the female component includes an open barrel having an outer surface and an inner surface, a female flange cap at one end of the open barrel, openings through the female flange cap, extending into a center of the open barrel, and a recessed tiedown bar that extends between the openings through the female flange cap. The method includes securing the ends of the suture at a dorsal side of the foot, with a knot secured against the recessed tiedown bar at the dorsal side of the foot. The tiedown bar provides an alterative position to secure the suture at the top of the phalanx bone, without a need to secure or tie the suture upon the phalanx bone itself.

Turning to the drawings, FIG. 1 illustrates an example metatarsal bone 1, proximal phalanx bone 2, and plantar plate 3 of the foot. FIG. 1 is provided as a representative illustration of certain parts of the foot, so that aspects of the embodiments can be described with reference to the parts of the foot. The example illustration of the metatarsal bone 1, proximal phalanx bone 2, and plantar plate 3 of the foot are not intended to be limiting, however, and the implants and methods of plantar plate repair described herein are applicable to phalanx bones of various sizes and shapes and various types of injuries to plantar plates.

The plantar plate 3 is a strong fibrocartilaginous structure which attaches the metatarsal bone 1 to phalanx bone 2, on the plantar side of the foot, at the joint between them. The plantar plate 3 is a main stabilizer of this joint in the sagittal plane. The plantar plate 3 also maintains the phalanx bone 2 in position with the metatarsal bone 1, preventing the phalanx bone 2 from drifting or over-extending. The plantar plate 3 is an extension of the plantar fascia, which is a connective tissue that supports the arch on the plantar side of the foot. The plantar fascia runs from the tuberosity of the calcaneus (heel bone) forward to the heads of the metatarsal bones.

The plantar plate 3 can be injured, such as by stretching, tearing, or separating (in whole or part) from the phalanx bone 2 or the metatarsal bone 1, or in other ways. Plantar plate tears are a relatively common injury that have been diagnosed more frequently in recent years. Plantar plate tears most commonly affect the second metatarsophalangeal joint, although other toes can be affected. Plantar plate tears can occur from a traumatic incident, such as a stubbing or twisting injury while running or hiking but are usually due to a progressive injury over time, resulting from certain foot biomechanics. Plantar plate tears are also more common for individuals with longer toes.

Symptoms of a plantar plate tears include pain at the joint, particularly with activity. In some cases, the injured toe will start to "hammer" or "float" and may no longer touch the ground in severe cases. Plantar plate tears can also permit injured toes to drift in the transverse plane. Conservative treatments for plantar plate injuries can be successful in certain patients and include immobilization, the use of stiff-soled shoes, the use of non-steroidal anti-inflammatory drugs (NSAIDs), and taping or splinting the toe. If conservative therapies fail, a surgical procedure may be more effective to repair the injury.

Figure 2:
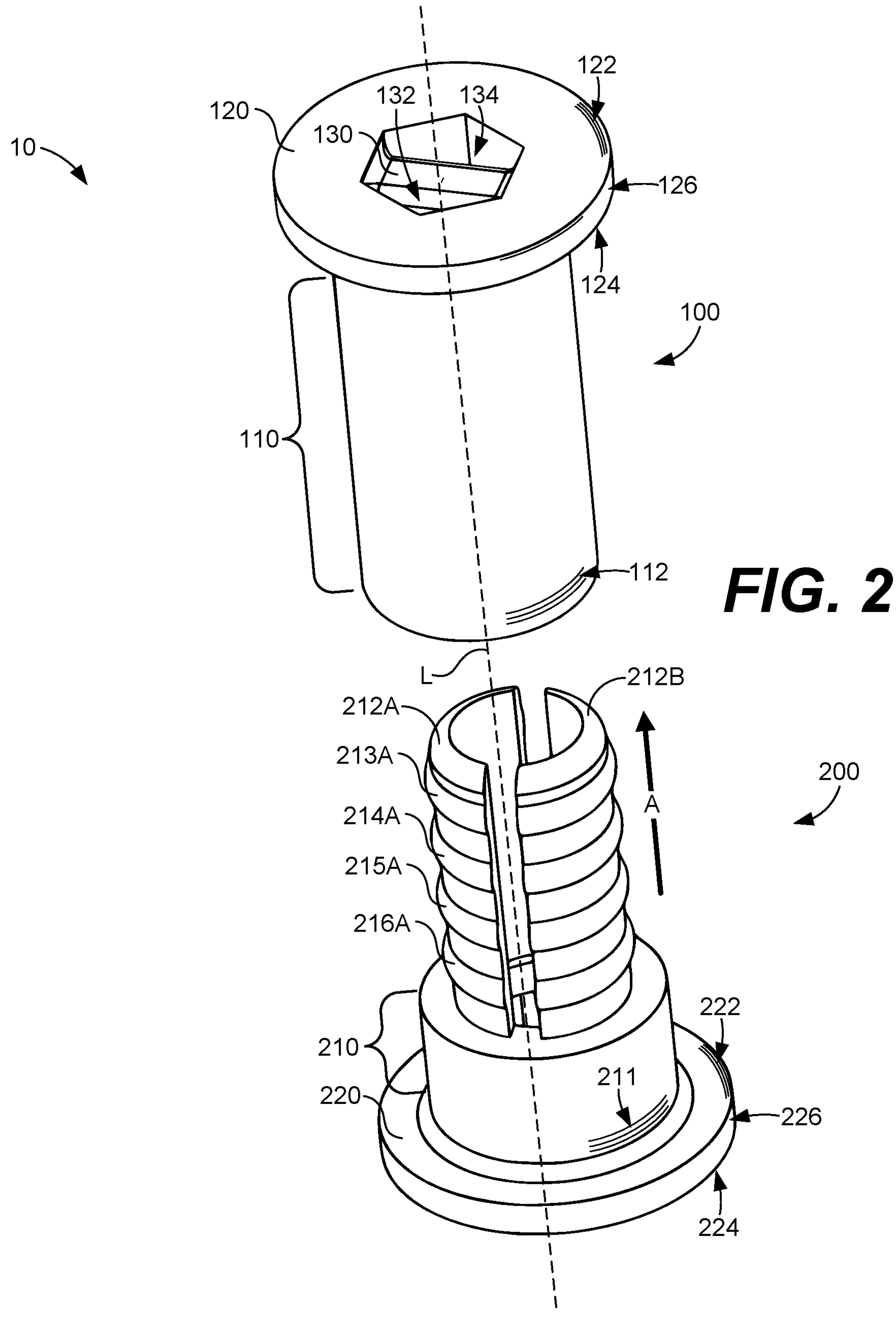
FIG. 2 illustrates an example implant for plantar plate repair according to various examples described herein.

FIG. 2 illustrates an example implant 10 for plantar plate repair according to various examples described herein. The implant 10 is illustrated as a representative example of the embodiments. The implant 10 is not necessarily drawn to scale in FIG. 1, and the implant can vary in shape and in size as compared to that shown. In some cases, the certain features of the implant 10 can be modified or altered without deviating from the scope of the embodiments. For example, the sizes, shapes, and relative spacings of certain features, such as the open barrels, flange caps, fingers, ribs, and other features of the implant 10 can be altered to some extent as compared to that shown.

The implant 10 includes a female component 100 and a male component 200. As described in further detail below, fingers of the male component 200 can snap and interlock into interlocking features within the open barrel of the female component 100. For example, the female component 100 can first be installed, from the dorsal side of the foot, into a hole drilled through the phalanx bone. The male component 200 can then be inserted in the direction "A" shown in FIG. 1, from the plantar side of the foot, into the hole drilled through the phalanx bone and into the open barrel of the female component 100, snapping the male component 200 into the open barrel of the female component 100.

Figure 3:
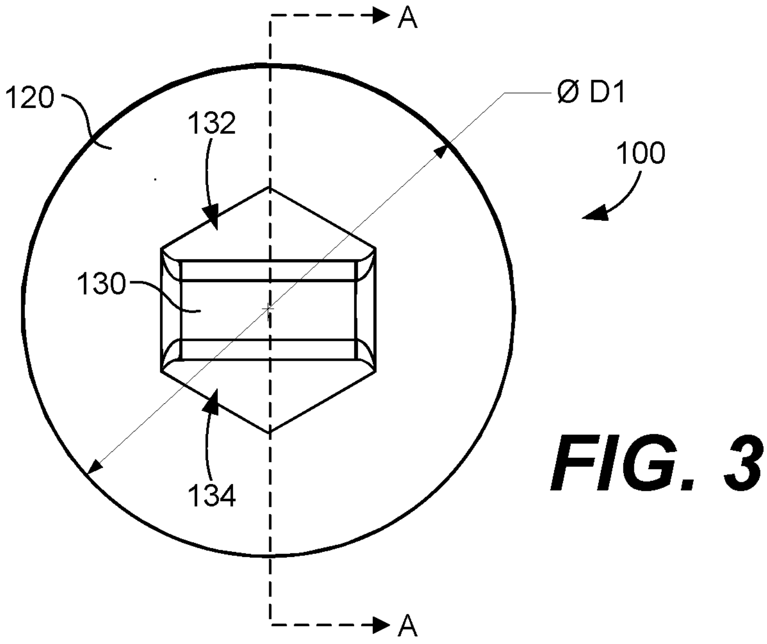
FIG. 3 illustrates an example top-down view of the female component of the implant shown in FIG. 2 according to various examples described herein.
Figure 4:
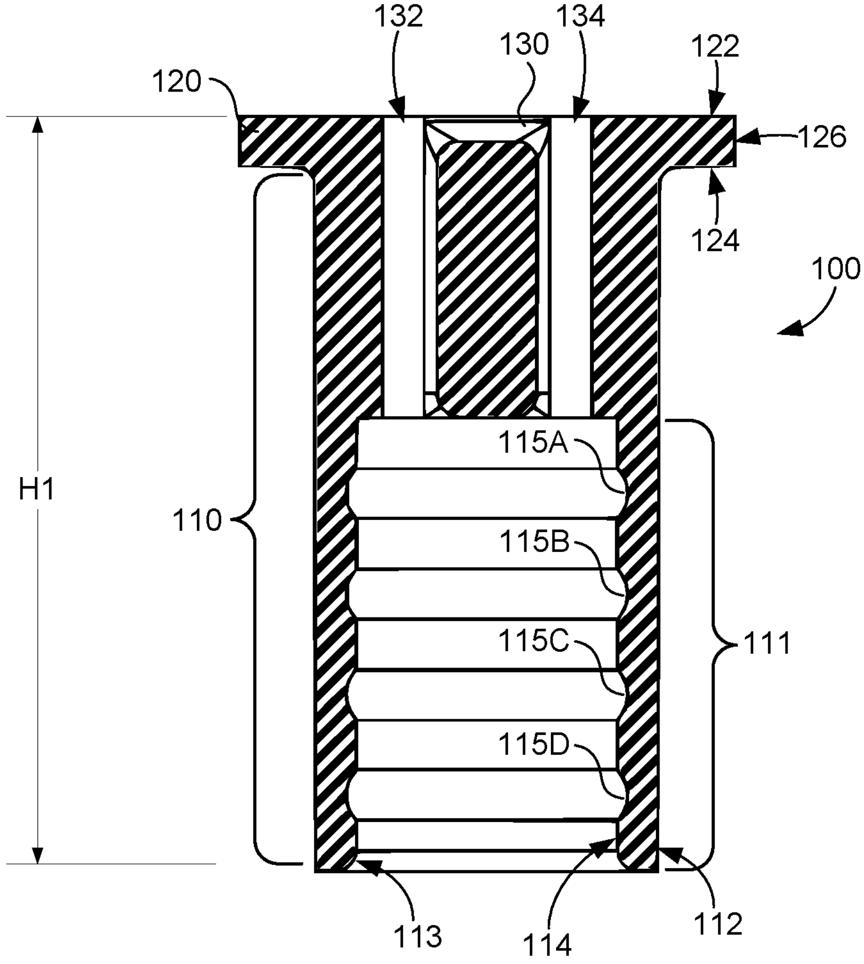
FIG. 4 illustrates a sectional view of the female component designated A-A in FIG. 3 according to various examples described herein.

The female component 100 includes an open barrel 110 having an outer surface 112 and an inner surface 114 (see FIG. 4). The female component 100 also includes a flange cap 120 at one end of the open barrel 110. The flange cap 120 has a top surface 122, a bottom surface 124, and an outer peripheral surface 126. The outer peripheral surface 126 of the flange cap 120 extends a radial distance away or apart from the central longitudinal axis "L" of the female component 100 further than the outer surface 112 of the open barrel 110, as shown in FIG. 2. The flange cap 120 also includes a recessed tiedown bar 130 that extends between openings 132 and 134 through the flange cap 120. Additional features of the female component 100 are described below with reference to FIGS. 3 and 4.

Figure 5:
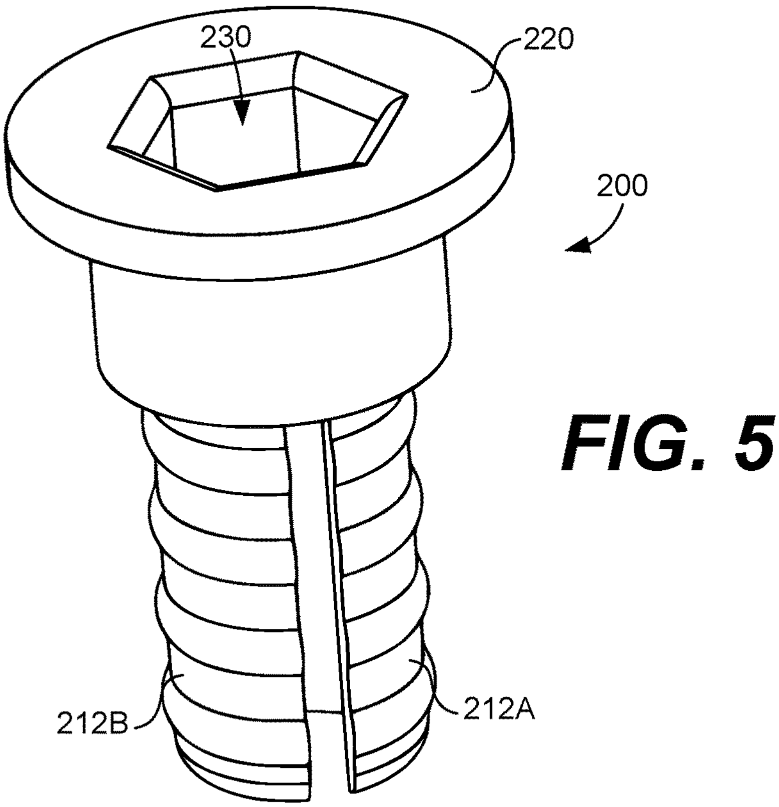
FIG. 5 illustrates a perspective view of the male component of the implant shown in FIG. 2 according to various examples described herein.

The male component 200 includes an open barrel portion 210, a pair of fingers 212A and 212B (collectively "fingers 212") extending from one end of the open barrel portion 210, and a flange cap 220 at another end of the open barrel portion 210. The flange cap 220 has a top surface 224, a bottom surface 222, and an outer peripheral surface 226. The outer peripheral surface 226 of the flange cap 220 extends a radial distance away or apart from the central longitudinal axis "L" of the male component 200 further than the outer surface 211 of the open portion barrel 210, as shown in FIG. 2. The flange cap 220 also includes an opening through the flange cap 220, as shown in FIG. 5 and described below. Additional features of the male component 200 are described below with reference to FIGS. 5 and 6.

Both the open barrel 110 of the female component 100 and the open barrel portion 210 of the male component 200 are cylindrical in shape in the example illustrated. The diameter or dimension of the open barrel 110 is designed to be the same as (within manufacturing tolerances) that of the open barrel portion 210 of the male component 200. The female component 100 and the male component 200 can be formed using a bio-durable implantable polymer, such as polyethylene, polyether ether ketone (PEEK), or other materials of sufficient strength and suitable use as a long-term implant. PEEK, for example, is strong enough to remain secured in place and anchor sutures for the plantar plate repair techniques described herein. PEEK is also flexible enough to permit the fingers 212 of the male component 200 to bend or deform to the extent needed for insertion into the open barrel 110 of the female component 100.

As shown in FIG. 2, the fingers 212A and 212B each extend separately from one end of the open barrel portion 210, with an open space between them. The fingers 212A and 212B are semi-circular in cross-section, taken in a plane perpendicular to the the longitudinal axis "L." The fingers 212A and 212B are flexible to some extent and can bend to a degree, inwardly, if compressed together. The fingers 212A and 212B are designed with features to fit and snap into the open barrel 110 of the female component 100.

In the example shown, the finger 212A includes a number of interlocking features, such as the ridges or ribs 213A-216A, which are evenly spaced along a length of the outer surface of the finger 212A. The finger 212B also includes a similar number of ridges or ribs. In other cases, the fingers 212A and 212B can include fewer or more ribs, and the ribs can be spaced or positioned in other ways as compared to that shown. The ribs 213A-216A on the finger 212A and those on the finger 212B act as a type of mechanical detent or a means to resist or arrest motion, in connection with the inner surface of the open barrel 110. The inner surface of the open barrel 110 also includes corresponding features for snapping and holding the fingers 212A and 212B in place, as described below with reference to FIG. 4.

FIG. 3 illustrates an example top-down view of the female component 100, and FIG. 4 illustrates a sectional view of the female component 100 designated A-A in FIG. 3. Referring to FIG. 4, the open barrel 110 includes the outer surface 112 and the inner surface 114. An interlock portion 111 of the open barrel 110 includes a number of interlocking features, such as the indentations 115A-115D along the inner surface 114. In the example shown, the indentations 115A-115D are evenly spaced along the inner surface 114, although the indentations 115A-115D can have other spacings. Also, a different number of the indentations 115A-115D can be relied upon as compared to that shown.

The fingers 212A and 212B of the male component 200 can be inserted into the interlock portion 111 of the open barrel 110 of the female component 100. As part of a surgical procedure for plantar plate repair described below, the fingers 212A and 212B of the male component 200 can be inserted into the interlock portion 111 of the female component 100, with both the female component 100 and the male component 200 being positioned within a hole drilled through the phalanx bone of the foot. The end of the open barrel 110 also includes a curved lip 113 to facilitate the insertion of the fingers 212A and 212B into the interlock portion 111 of the open barrel 110. The fingers 212A and 212B can also include a curved or beveled leading surface or edge, and a curved lip 213 of the finger 212B is identified in FIG. 6. The finger 212A also includes a similar curved lip.

Depending on certain conditions, such as the size of the phalanx bone, the fingers 212A and 212B can be inserted to a greater or lesser extent into the interlock portion 111 of the open barrel 110. For example, the fingers 212A and 212B can be inserted to such an extent that the rib 213A (FIG. 3) is seated into the indentation 115D, the indentation 115C, the indentation 115B, or the indentation 115A. In other words, the fingers 212A and 212B can be partly or fully extended within the interlock portion 111 of the open barrel 110 to account for different sizes (e.g., diameters) of phalanx bones or other conditions. In any case, the fingers 212A and 212B can seat securely within the interlock portion 111, and the female component 100 and the male component 200 can also be secured in place together with a suture as described herein.

Referring between FIGS. 3 and 4, the openings 132 and 134 are shown to extend through the flange cap 120 and into the open barrel 110. The recessed tiedown bar 130 also extends between the openings 132 and 134. Suture passing wires can be extended through the openings 132 and 134, and lengths (e.g., opposite ends) of a sterile surgical thread or suture can be pulled back through the openings 132 and 134. The two ends of the suture can be tied together at a position over the tiedown bar 130 and secured against the tiedown bar 130, with the knot being recessed to a position below the top surface 122 of the flange cap 120. The tiedown bar 130 provides an alterative position to secure the suture at the top of the phalanx bone, without a need to secure or tie the suture upon the phalanx bone itself.

Certain dimensions of the female component 100 are shown in FIGS. 3 and 4. For example, the height H1 of the female component 100, measured from the top surface 122 of the flange cap 120 to the end of the open barrel 110, is identified. Additionally, the diameter D1 of the flange cap 120 is also identified. An example dimension of H1 is 8.5 mm and an example dimension of D1 is 5 mm in one case, although H1 can range from 5-10 mm and D1 can range from 3-7 mm, or larger ranges. The distance or space between the top surface 122 and the bottom surface 124 of the flange cap 120 can be 0.5 mm in one example, although larger or smaller sizes can be used.

Figure 6:
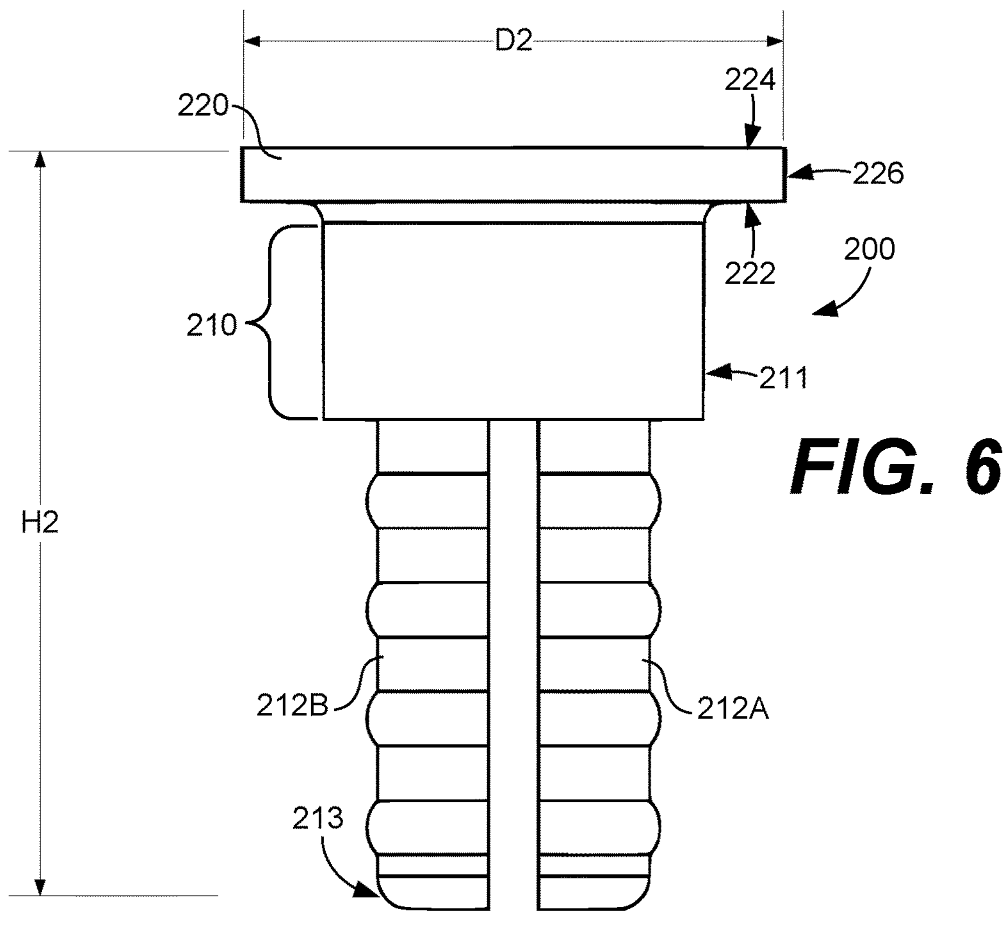
FIG. 6 illustrates a side view of the male component of the implant shown in FIG. 2 according to various examples described herein.

FIG. 5 illustrates a perspective view of the male component 200 of the implant 10 shown in FIG. 2, and FIG. 6 illustrates a side view of the male component 200. As shown, the flange cap 220 includes an opening 230, which extends through a center of the flange cap 220 and the center of the open barrel portion 210, to a position between the fingers 212. When installed in a hole drilled through the phalanx bone, the flange cap 220 will rest upon the bottom surface of the phalanx bone, at the plantar side. Ends of a surgical thread or suture can be pulled through the opening 230 and between the fingers 212 and, ultimately, through the female component 100, as further described below.

Certain dimensions of the female component 100 are shown in FIG. 6. For example, the height H2 of the male component 200, measured from the top surface 224 of the flange cap 220 to the end of the fingers 212, is identified. Additionally, the diameter D2 of the flange cap 220 is also identified. An example dimension of H2 is 7.5 mm and an example dimension of D2 is 5 mm in one case, although H2 can range from 5-10 mm and D2 can range from 3-7 mm, or larger ranges. The distance or space between the top surface 224 and the bottom surface 222 of the flange cap 220 can be 0.5 mm in one example, although larger or smaller sizes can be used.

Figure 7:
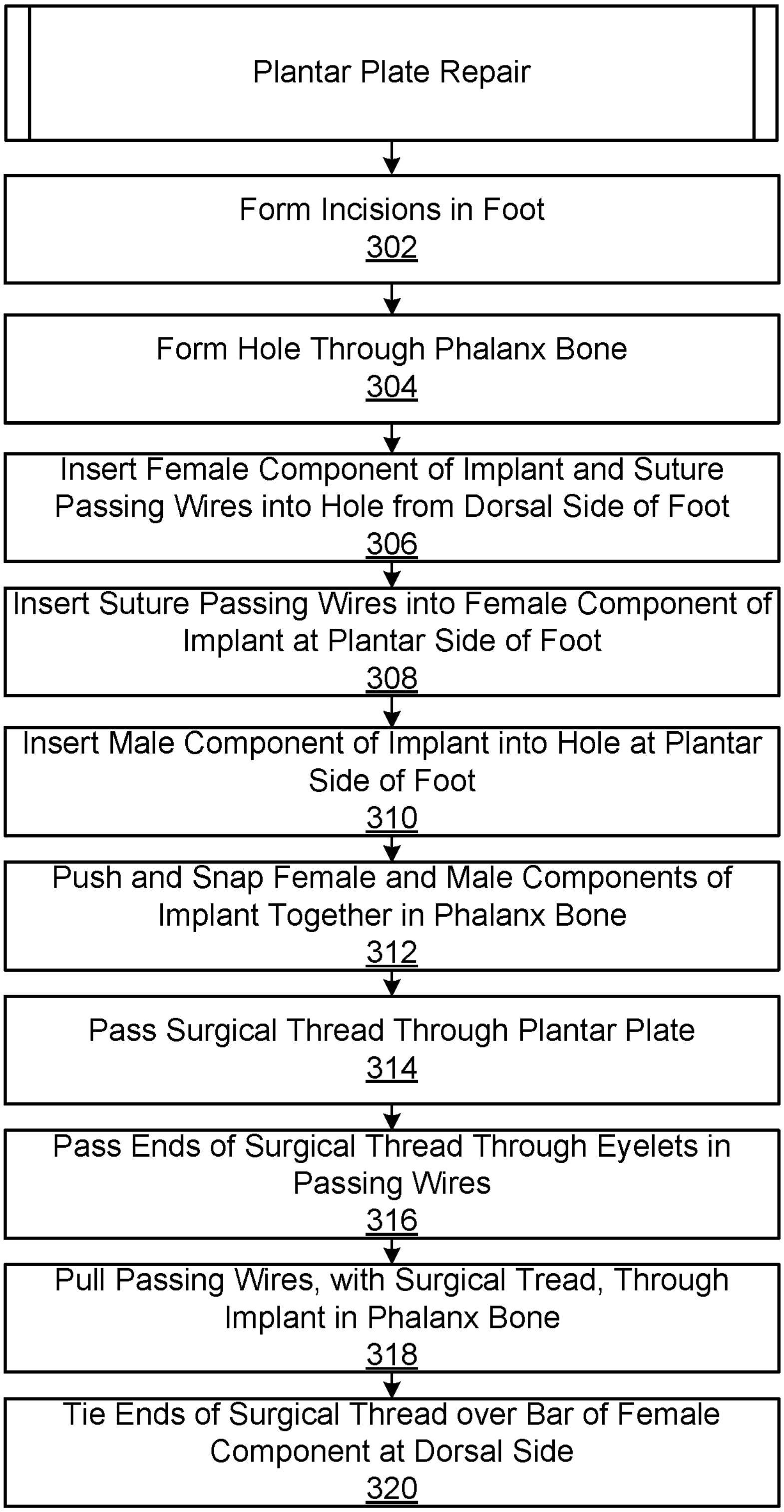
FIG. 7 illustrates steps in a method of plantar plate repair using the implant shown in FIG. 2 according to various examples described herein.

Turning to other aspects of the embodiments, FIG. 7 illustrates steps in a method of plantar plate repair using the implant 10 shown in FIG. 2 according to various examples described herein. The method is provided as a representative example. The relative sizes of the bones, the implant, and other features are not necessarily drawn to scale, and the relative sizes can vary in practice. The order of the steps can vary as compared to that shown and described in some cases. Additionally, certain steps can be omitted entirely in some cases, depending on the procedure or circumstances, and additional steps can also be taken where necessary.

Starting at reference numeral 302, the process includes a surgeon making or forming incisions in the foot at a location where the plantar plate repair is needed. For example, for a plantar plate repair at the joint between the second metatarsal and the second proximal phalanx bone, a first incision would be made on the dorsal side of the foot above the joint and a second incision would be made on the plantar side of the foot below the joint. The incisions can be made to the extent or length needed to provide sufficient access for the repair, such as to open an area above and below the joint. Any suitable surgical tools can be relied upon to make the first and second incisions.

Figure 8:
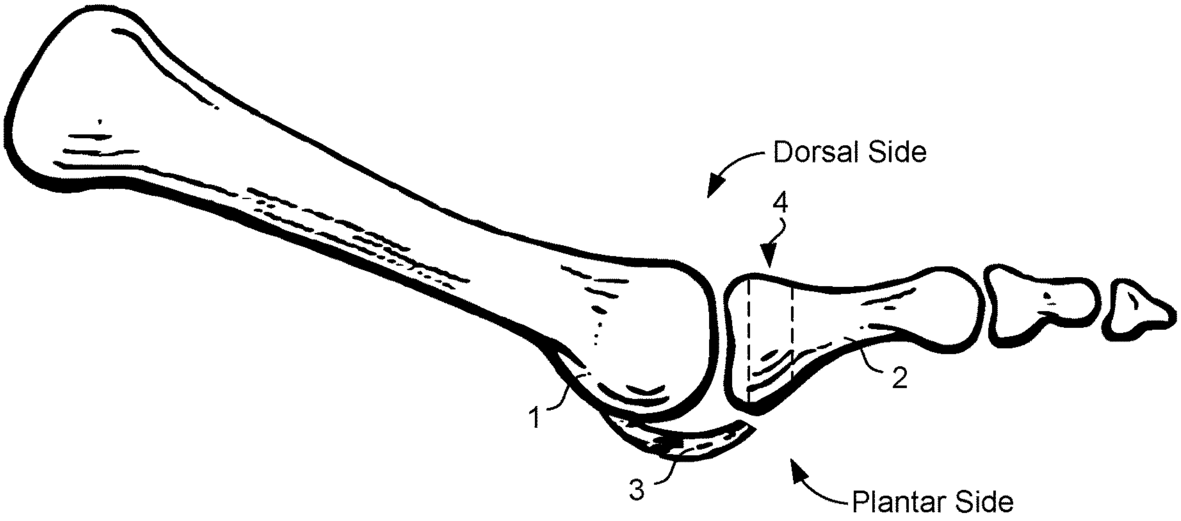

At reference numeral 304, the process includes forming a hole in the proximal phalanx bone. Referring to FIG. 8 as an example, the surgeon can drill the hole 4 through the phalanx bone 2, starting from either from the dorsal side or the plantar side, and a pilot hole can be drilled first, followed by a final hole in some cases. Any suitable surgical tools can be relied upon to form the hole 4, and the position of the hole 4 can be determined by the surgeon at the time of the repair, although a position close to the joint can be preferred in most cases. The size or diameter of the hole 4 can be selected to be large enough to accommodate the diameters of the open barrel 110 of the female component 100 and the open barrel portion 210 of the male component 200, with sufficient clearance to insert the implant 10 into the hole 4.

Figure 9:
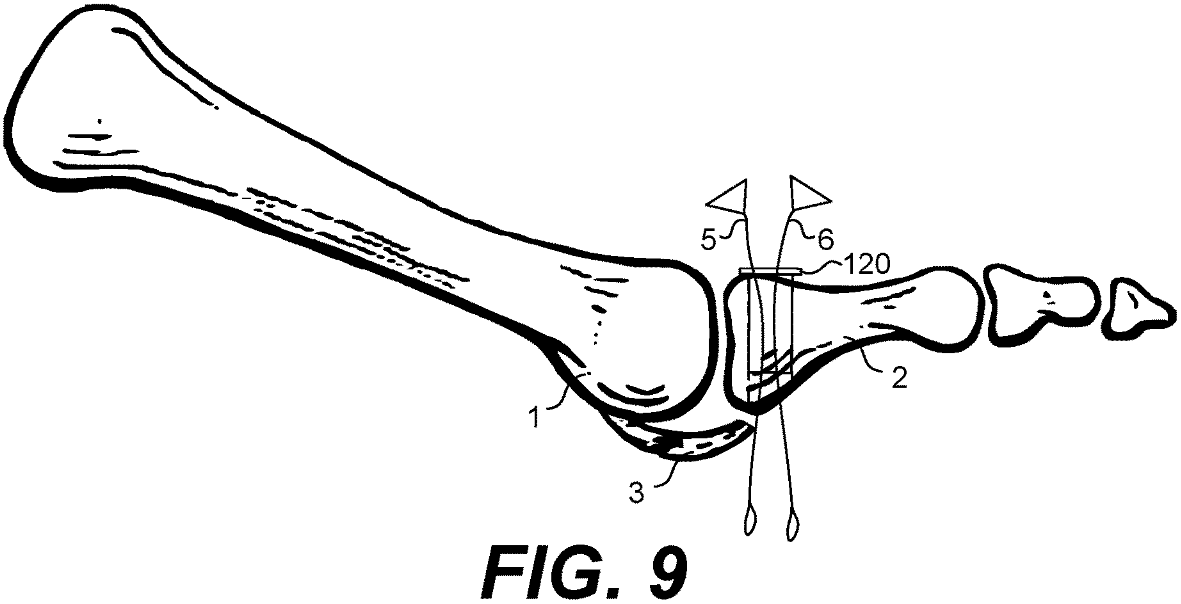

At reference numeral 306, the process includes the surgeon inserting the female component 100 of the implant 10 into the hole 4 in the phalanx bone 2 from the dorsal side of the foot, as shown in FIG. 9. The flange cap 120 of the female component 100 can rest upon the top surface of the phalanx bone 2 once fully inserted. At reference numeral 308, the process includes the surgeon inserting suture passing wires 5 and 6 through the openings 132 and 134 (see FIG. 2) of the female component 100 and through the hole 4 in the phalanx bone 2, from the dorsal side of the foot, so that the suture passing wires 5 and 6 extend to the plantar side of the foot, as also shown in FIG. 9. In some cases, the female component 100 can be pre-loaded with the suture passing wires 5 and 6, and the steps at reference numerals 306 and 308 can be performed together with the insertion of the female component 100 and the suture passing wires 5 and 6 through the hole 4 at the same time.

At reference numeral 310, the process includes the surgeon inserting the male component 200 of the implant 10 into the hole 4 through the phalanx bone 2, from the plantar side of the foot. Before doing so, the surgeon can also insert the passing wires 5 and 6 to extend between the fingers 212 and through the opening 230 of the flange cap 220 of the male component 200. The surgeon can then insert the male component 200 of the implant 10 into the hole 4, from the plantar side of the foot.

Figure 10:
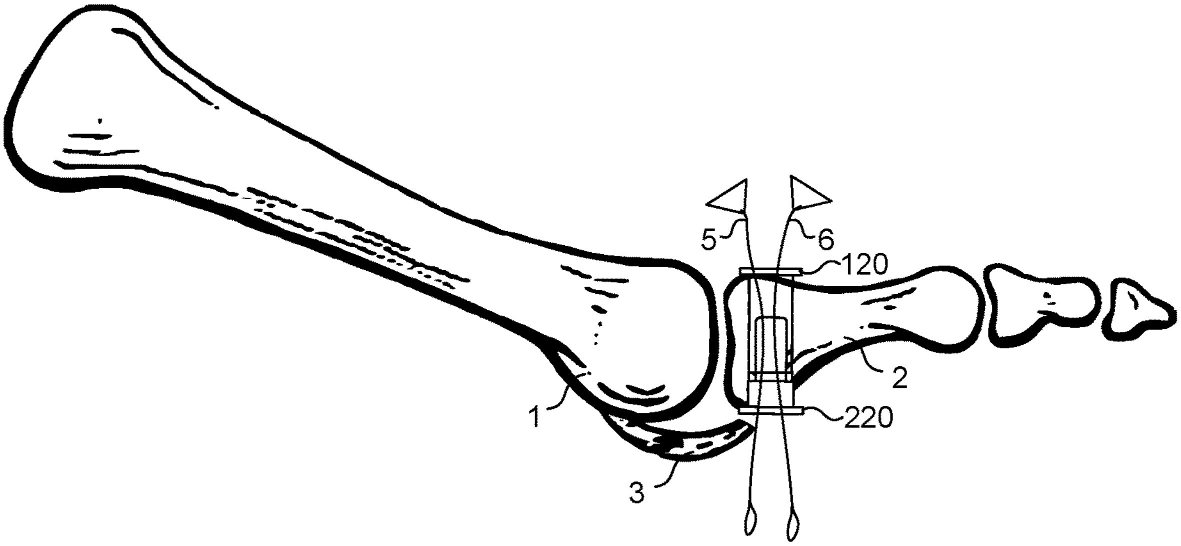

At reference numeral 312, the process also includes the surgeon holding the female component 100 in place from the dorsal side of the foot and pushing and snapping the fingers 212 of the male component 200 into the open barrel 110 of the female component 100, securing the male component 200 and the female component 100 together, as shown in FIG. 10. Here, the fingers 212 of the male component 200 are inserted into the interlock portion 111 of the female component 100 (see FIG. 4). The ridges or ribs 213A-216A of the fingers 212 (see FIG. 2) can seat and interlock into the indentations 115A-115D (see FIG. 4) along the inner surface 114 of the female component 100. The male component 200 and the female component 100 can snap together to the extent possible depending on the size of the phalanx bone 2, until the flange cap 220 of the male component 200 rests upon the bottom surface of the phalanx bone 2.

Figure 11:
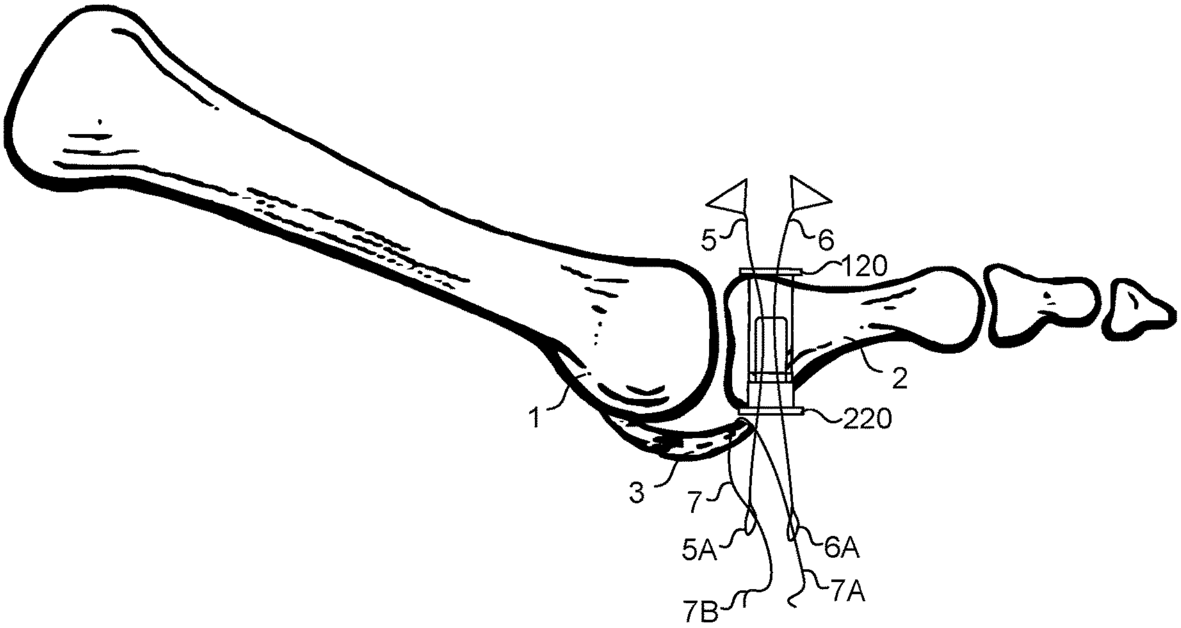

At reference numeral 314, the process includes the surgeon passing or threading a suture 7 through the plantar plate 3, as shown in FIG. 11. A surgical needle of any suitable type, for example, can be used to thread the suture 7 through the plantar plate 3. The suture 7 can be threaded through the plantar plate 3 at any suitable location based on the judgment of the surgeon at the time of the procedure. At reference numeral 316, the process includes the surgeon passing or threading the respective ends 7A and 7B of the suture 7 through the eyelets 5A and 6A of the passing wires 5 and 6, respectively.

Figure 12:
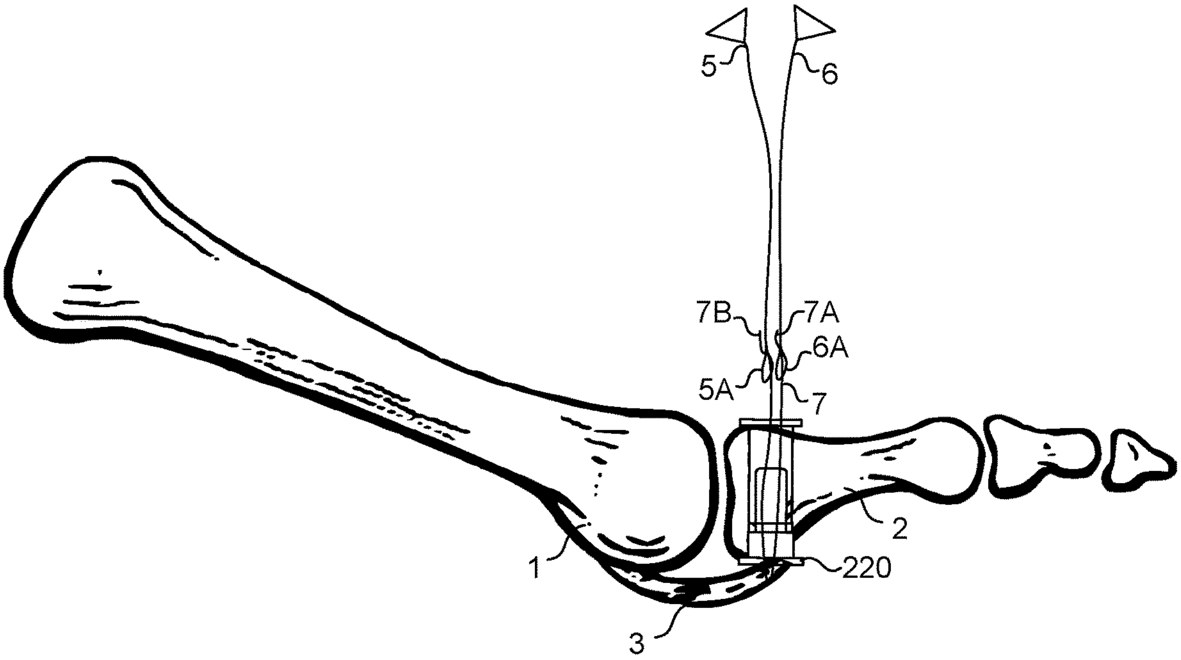
Figure 13:
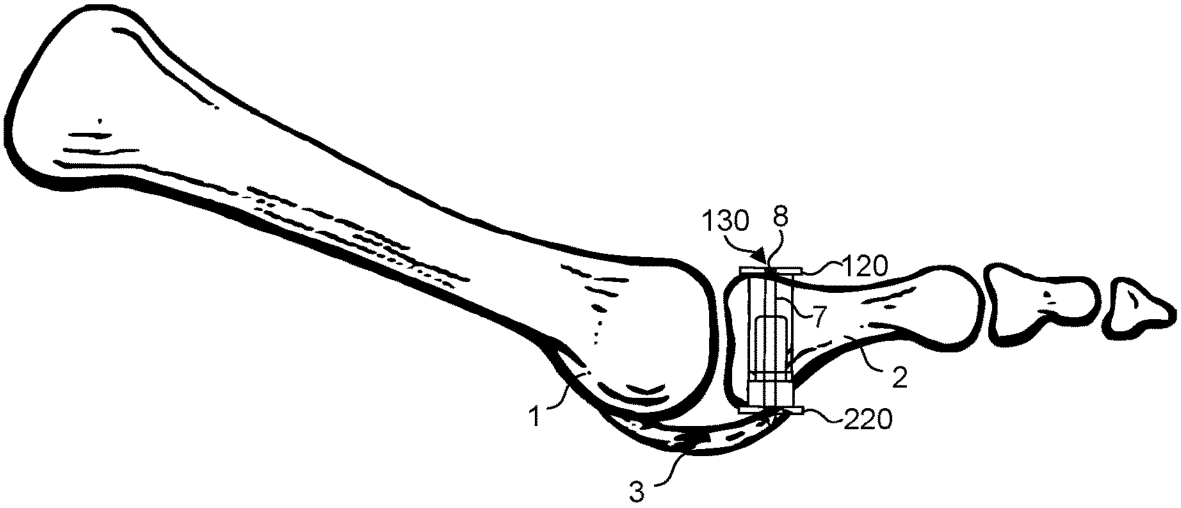

At reference numeral 318, the process includes the surgeon pulling the passing wires 5 and 6 through the implant 10 in the phalanx bone 2, as shown in FIG. 12, along with the ends 7A and 7B of the suture 7. In this step, the ends 7A and 7B of the suture 7 are pulled through the opening 230 in the male component 200, through the open barrel portion 210 of the male component 200, between the fingers 212 of the male component 200, through the open barrel 110 of the female component 100, and through the openings 132 and 134 of the female component 100. The ends 7A and 7B of the suture 7 are pulled through respective ones of the openings 132 and 134, as the passing wires 5 and 6 were inserted through the openings 132 and 134 separately. The ends 7A and 7B of the suture 7 then extend to the dorsal side of the foot as shown in FIG. 12. The plantar plate 3 is also pulled and secured against the flange cap 220 of the male component 120, where it is held in place at the plantar side of the foot.

At reference numeral 320, the process includes the surgeon tieing the ends 7A and 7B of the suture 7 together into a knot 8 over the recessed tiedown bar 130 (see FIG. 2) in the flange cap 120 of the female component 100. The remaining lengths of the the ends 7A and 7B of the suture 7 can then be cut off. Thus, the plantar plate 3 can be secured to the implant 10 using sutures, secured to the plantar plate by a surgeon, who then passes them through the implant 10 and tensions and secures the plantar plate 3 and implant 10 with one or more knots. The knots can be placed on the dorsal aspect over the recessed tiedown bar 130 of the implant 10. The suture passing wires 5 and 6 can be provided with each implant 10, so that the surgeon only has to pass the the ends 7A and 7B of the suture 7 through the eyelets 5A and 6A of the passing wires 5 and 6, respectively, which can then be pulled through the implant 10.

Example dimensions of the implant 10 are described above. In one approach, the implant 10 does not take up more than a third of the diameter of the phalanx bone 2. Thus, a diameter of 3.5 mm was chosen, as one example, to accommodate the average reported anatomical sizes of phalanx bones. Instead of creating multiple implants for varying bone heights, the implant 10 can accommodate multiple heights, ranging from 9 mm to 12 mm in height, for example. The recessed tiedown bar 130, which carries most of the load from the suture tension, is approximately 1.45 mm in width, 2.5 mm in length, and 3.25 mm in depth, in one example, although other sizes can be used.

Other approaches were considered, including outer threading, inner threading, and one-piece implants. However, because of the size of the implant 10 and the relative porosity of phalanx bones, a one-piece implant may not be able to hold under the amount of tension. The final design described herein includes two pieces, a male component and a female component, with a snap fit connection between them. The snap fit provides reassurance to a surgeon that the female and male components lock into place with each other.

For the surgical method, several approaches were considered to insert the implant 10. These included a single dorsal incision, a single plantar incision, or an incision on the plantar side with a small dorsal incision. Although other methods can be relied upon, one method is to approach from both the plantar and dorsal side to secure the device through the proximal phalanx. This will eliminate the need for a metatarsal osteotomy and will give the surgeon the necessary space to complete the procedure.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

The invention claimed is:

1. An implant for plantar plate repair, comprising:
- a female component, the female component comprising:
  - an open barrel having an outer surface and an inner surface;
  - a female flange cap at one end of the open barrel;
  - openings through the female flange cap, extending into a center of the open barrel; and
  - a recessed tiedown bar that extends between the openings through the female flange cap; and
- a male component, the male component comprising:
  - an open barrel portion having an outer surface;
  - a pair of fingers extending from one end of the open barrel portion;
  - a male flange cap at another end of the open barrel portion; and
  - an opening through the male flange cap, extending into the open barrel portion.

2. The implant according to claim 1, wherein the female component further comprises female interlocking features formed into at least a portion of the inner surface of the female component.

3. The implant according to claim 2, wherein the male component further comprises male interlocking features formed into outer surfaces of the pair of fingers.

4. The implant according to claim 3, wherein the male interlocking features snap and interlock into the female interlocking features within the open barrel of the female component.

5. The implant according to claim 1, wherein an outer peripheral surface of the male flange cap extends a radial distance away from a central longitudinal axis of the male component further than the outer surface of the open barrel portion.

6. The implant according to claim 1, wherein an outer peripheral surface of the female flange cap extends a radial distance away from a central longitudinal axis of the female component further than the outer surface of the open barrel.

7. The implant according to claim 1, wherein the female component and the male component are formed from polyether ether ketone (PEEK).

8. A method of plantar plate repair, comprising:
- installing an implant for plantar plate repair according to claim 1 into a phalanx bone of a foot;
- passing a suture through a plantar plate at a plantar side of the foot;
- passing ends of the suture through the implant; and
- securing the ends of the suture at a dorsal side of the foot, with a knot secured against the implant at the dorsal side of the foot.

9. The method of claim 8, wherein installing the implant comprises:
- forming an incision in the dorsal side of a foot above the phalanx bone and in the plantar side of the foot below the phalanx bone;
- drilling a hole through the phalanx bone;
- inserting a female component of a plantar repair implant into the phalanx bone, from the dorsal side of the foot; and
- pushing the male component, from the plantar side, toward the female component, to snap the male component into the female component.

10. The method of claim 9, wherein installing the implant further comprises:
- inserting suture passing wires through the female component from the dorsal side, extending to the plantar side of the foot;
- sliding the suture passing wires through the male component of the plantar repair implant, at the plantar side;
- holding the female component in place from the dorsal side; and
- pushing the male component, from the plantar side, toward the female component, to snap the male component into the female component, with the suture passing wires extending through the implant.

11. The method of claim 10, further comprising:
- passing ends of the suture through the suture passing wires at the dorsal side of the foot; and
- pulling the ends of the suture through the implant using the suture passing wires.

12. The method of claim 8, wherein:
- the implant comprises a female component and a male component; and
- the female component comprises:
  - an open barrel having an outer surface and an inner surface;
  - a female flange cap at one end of the open barrel;
  - openings through the female flange cap, extending into a center of the open barrel; and
  - a recessed tiedown bar that extends between the openings through the female flange cap.

13. The method of claim 12, wherein securing the ends of the suture comprises securing the ends of the suture at a dorsal side of the foot, with a knot secured against the recessed tiedown bar at the dorsal side of the foot.

14. The method of claim 12, wherein the male component comprises:
- an open barrel portion having an outer surface;
- a pair of fingers extending from one end of the open barrel portion;
- a male flange cap at another end of the open barrel portion; and
- an opening through the male flange cap, extending into the open barrel portion.

15. The method of claim 14, wherein:
- the female component further comprises female interlocking features formed into at least a portion of the inner surface of the female component;
- the male component further comprises male interlocking features formed into outer surfaces of the pair of fingers; and
- installing the implant comprises snapping the male interlocking features into the female interlocking features.

16. An implant for plantar plate repair, comprising:
- a female component, the female component comprising:
  - an open barrel having an outer surface and an inner surface;
  - a female flange cap at one end of the open barrel; and
  - a recessed tiedown bar,
  - wherein the female component further comprises female interlocking features formed into at least a portion of the inner surface of the female component; and
- a male component, the male component comprising:
  - an open barrel portion having an outer surface; and
  - a male flange cap at another end of the open barrel portion, wherein the male component further comprises a pair of fingers, the pair of fingers comprising male interlocking features formed into outer surfaces of the pair of fingers.

17. The implant according to claim 16, wherein the male interlocking features snap and interlock into the female interlocking features within the open barrel of the female component.

18. The implant according to claim 16, wherein:
- an outer peripheral surface of the male flange cap extends a radial distance away from a central longitudinal axis of the male component further than the outer surface of the open barrel portion; and
- an outer peripheral surface of the female flange cap extends a radial distance away from a central longitudinal axis of the female component further than the outer surface of the open barrel.

* * * * *